US008512261B2

(12) United States Patent
Diniz Zanetti et al.

(10) Patent No.: US 8,512,261 B2
(45) Date of Patent: Aug. 20, 2013

(54) PERINEAL ELASTICITY METER

(76) Inventors: Miriam R. Diniz Zanetti, Sao Paulo (BR); Mary Nakamura, Sao Paulo (BR)

( * ) Notice: Subject to any disclaimer, the term of this patent is extended or adjusted under 35 U.S.C. 154(b) by 486 days.

(21) Appl. No.: 12/666,719

(22) PCT Filed: Jun. 25, 2008

(86) PCT No.: PCT/BR2008/000178
§ 371 (c)(1),
(2), (4) Date: Dec. 24, 2009

(87) PCT Pub. No.: WO2009/000056
PCT Pub. Date: Dec. 31, 2008

(65) Prior Publication Data
US 2010/0185123 A1 Jul. 22, 2010

(30) Foreign Application Priority Data
Jun. 26, 2007 (BR) ........................... 0702130

(51) Int. Cl.
A61B 5/103 (2006.01)
A61B 5/117 (2006.01)
A61B 1/32 (2006.01)
A61B 1/00 (2006.01)
G01B 1/00 (2006.01)
G01B 3/00 (2006.01)
G01B 5/00 (2006.01)

(52) U.S. Cl.
USPC ........... 600/588; 600/201; 600/219; 600/220; 600/587; 600/591; 33/511; 33/512; 33/542; 33/542.1

(58) Field of Classification Search
USPC .................... 33/446, 501.04, 501.08, 501.12, 33/501.5, 511, 512, 542–545, 555.1–555.4, 33/558.01, 755–770; 600/201, 202, 218–235, 600/587, 588, 591
See application file for complete search history.

(56) References Cited

U.S. PATENT DOCUMENTS 7,527,601 B2 * 5/2009 Dubey et al. .................. 600/588
2008/0177204 A1 * 7/2008 Greenberg .................... 600/588

* cited by examiner

*Primary Examiner* — Sean P Dougherty
*Assistant Examiner* — Devin Henson
(74) *Attorney, Agent, or Firm* — Arent Fox LLP

(57) ABSTRACT

A Perineal elasticity meter having a circular central stem marked with millimeter markings and a sleeve portion surrounding the circular stem. Hinges connect the sleeve to expanders that extend from the circular stem. The perineal elasticity meter is configured to be inserted into the vagina of a patient in order to measure the elasticity of the perineal area. The sleeve includes an opening that shows a circumferential measurement achieved by the expansion of the expanders, as the sleeve moves along the central stem. Another perineal elasticity meter includes two stems connected via a hinge at a proximal portion of the stems. The proximal portions of the stems are configured to be inserted into the vagina of a patient and a measurement is taken of a distance between the expanded distal portion of the stems, thereby measuring the elasticity of the perineal area.

9 Claims, 3 Drawing Sheets

PERINEAL ELASTICITY METER

CROSS-REFERENCE TO RELATED APPLICATION

This application is a National Stage entry of International Application No. PCT/BR2008/000178, filed Jun. 25, 2008, which claims priority to Brazilian Application No. 018080032067, filed May 27, 2008, and Brazilian Application No. PI0702130-5, filed Jun. 26, 2007, the entire specification claims and drawings of which are incorporated herewith by reference.

Aspects presented herein provide a perineal elasticity meter, to be used in labor, in order to evaluate if an episiotomy to a childbearing woman will be necessary during the expulsive period of childbirth.

In the past, episiotomies were routinely used. However, modern studies have shown that episiotomies can cause additional complications such as infections, pain, sexual and urinary dysfunctions and genital prolapses.

The pelvic floor muscles, known as the perineum or perineal area, endure a tremendous strain on their capacity in order to enable a baby passage during the expulsive period of labor. The distensibility or elasticity of this muscle vary significantly from one woman to another. Thus, some women require an episiotomy and other do not.

Currently, the ability of the perineum to expand is made in an evaluation by the professional person assisting the childbearing woman in an empiric manner, without any objective evidence.

Devices having a vaginal inflatable balloon exist, the purpose of which is to stiffen the pelvic floor muscles. Devices also exist whose purpose is to strain the muscle through inflatable balloon in order to increase the pelvic floor elasticity. Nevertheless, a need remains for an instrument that evaluates the strain capacity of this muscle in a quantitative way.

In order to address these needs, aspects of a perineal elasticity meter are presented herein. This device will be used before the expulsive period of childbirth. The device is used by introducing it into the middle third portion of the vagina. Once inserted, the meter will be opened and measurement component indicates a diameter measurement of the gap. When this measure is longer than 12 cm, for example, the measurement provides an indication that the patient will not need an episiotomy.

A second example device operates in a similar manner, and is configured to be used before the expulsive period of childbirth. It is, also, configured to be inserted into the middle third portion of the vagina. However, the second example device differs from the first example model, in that this device will be configured to open only in an anterior-posterior direction. After the device is opened in the anterior-posterior direction, a millimeter measuring component will precisely show the gap measurement.

The perineal elasticity meter, as described herein, could comprise a material that can be sterilized after each use, and can also comprise a disposable material that can be disposed of after use.

Figure 1:
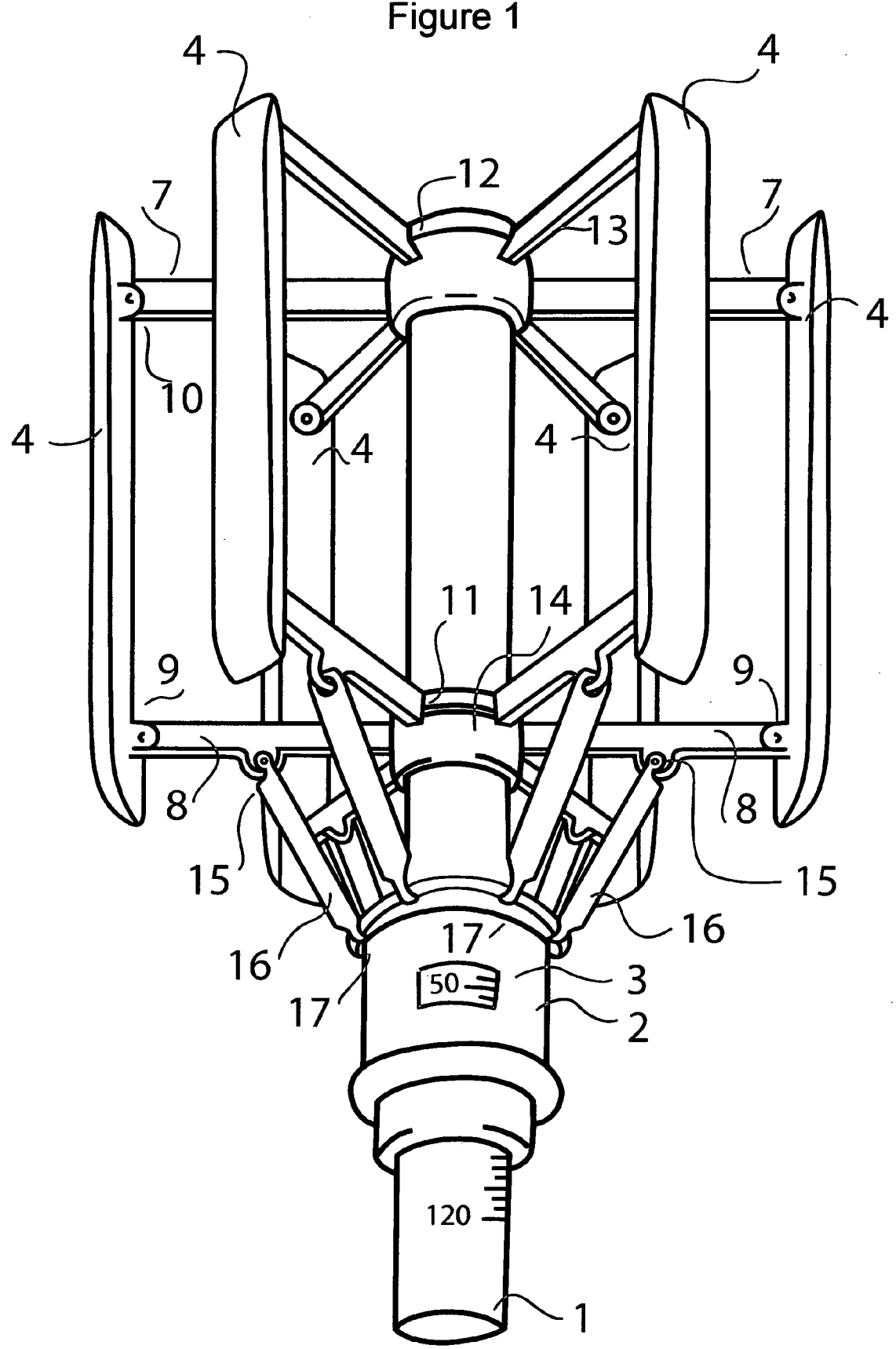
FIG. 1 shows a first embodiment of the present invention.

As seen in FIG. 1, the arms 7 and 8 are fixed in their medial face by hinges 11 and 12, the hinges 11, 12 being linked to two rings 13 and 14 fixed in the central stem 1. The arms 7 and 8 are connected at hinges 9 and 10 to expanders 4. Arm 8, also connects to a hinge 15 which connects to arm 16 that has its distal end connected to sleeve 2 through hinge 17.

Thus, when pressure is applied to the sleeve 2, it demonstrates the circumference measurement through window 3 and applies pressure to arm 16 that in turn applies pressure to arms 7 and 8 which expand the expanders 4 opening the circumference of the device to a maximum of, e.g., 12 centimeters in diameter.

Figure 2:
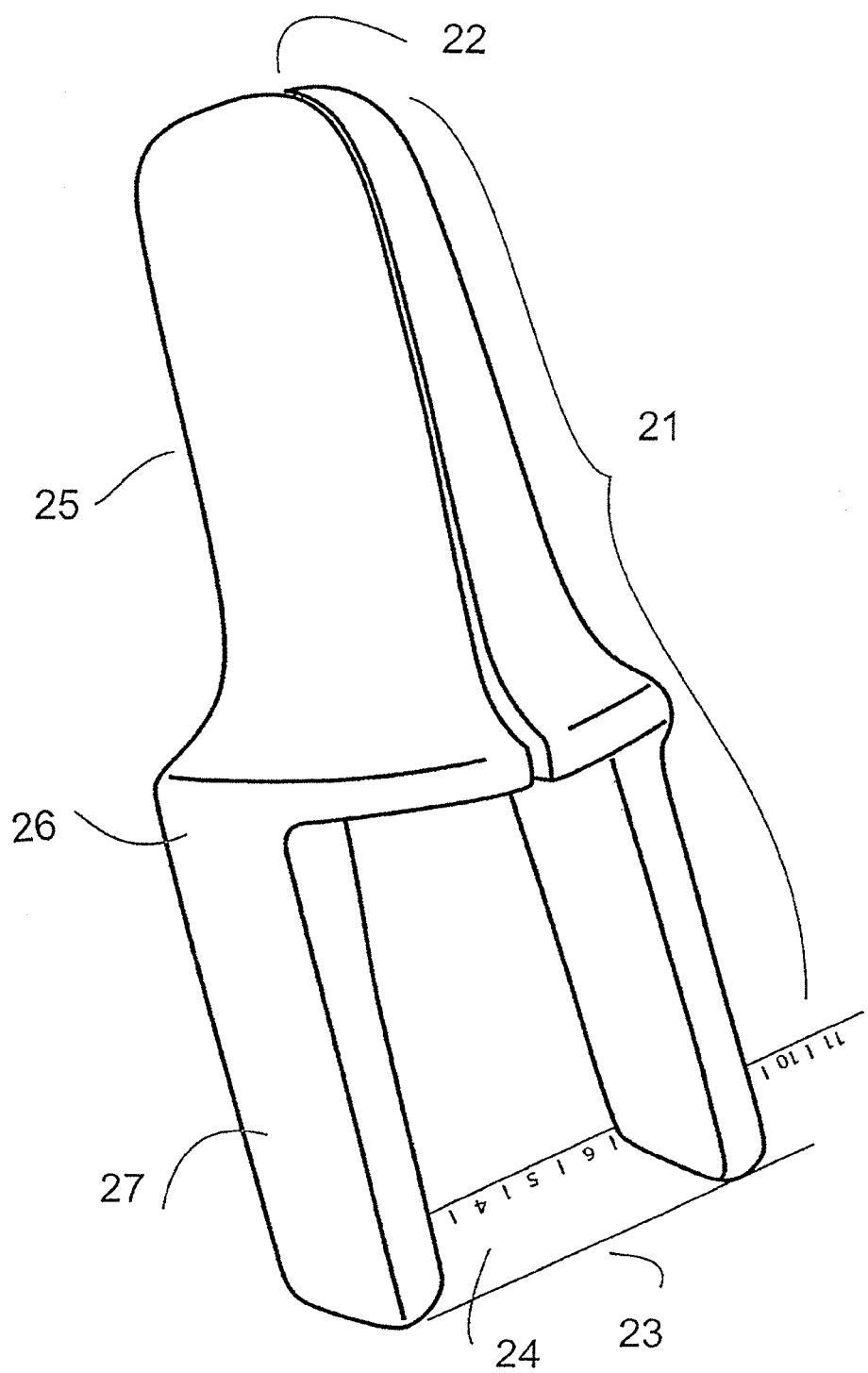
FIG. 2 shows a perspective view of a second embodiment in a relatively closed state.
Figure 3:
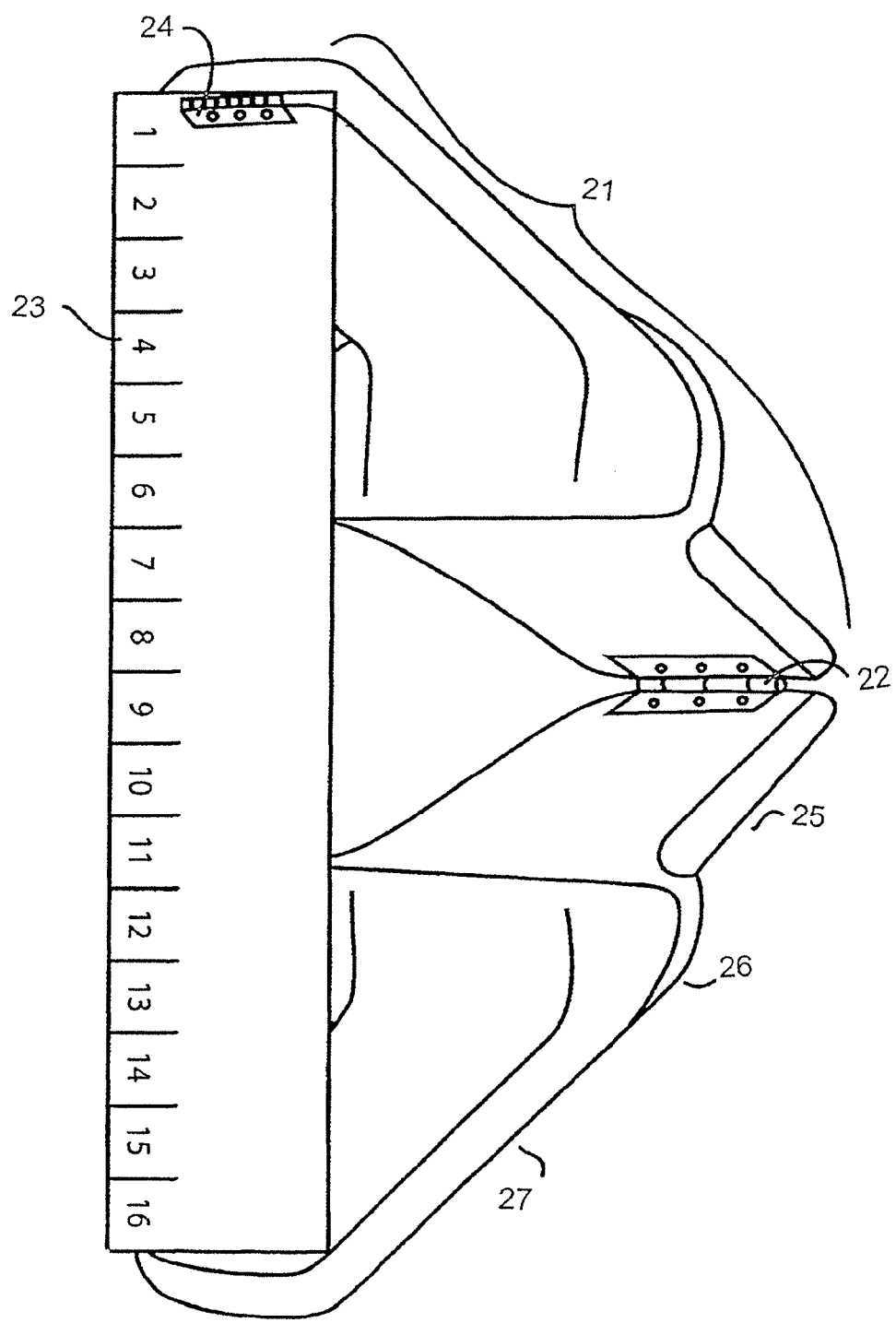
FIG. 3 shows a perspective view of the second embodiment in an open state.

Aspects of a second example model are shown in perspective (FIG. 2) and in an open state (FIG. 3). The second example includes two stems 21 that are fixed in their proximal extremities (or internal) through hinge 22. In the distal (or external) extremity, there is a millimeter ruler 23, e.g., a measurement component. The measurement component can be either fixed or can be configured to move relative to the stem via hinge 24. The stems 1 can be configured to have a form similar to gynecological speculum in their external face (convex surfaces) until approximately a middle of their extensions 25. The portion shaped similar to a speculum, or having a convex shape, finishes in a border 26 that limits the penetration of the device. The stems continue to extend beyond the border 26, in planar surfaces 27 configured to be grasped by the hands of the examiner.

A test performed with a perineal elasticity meter according to aspects presented herein, could be perceived by the patient similar to a gynecological specular exam. However, the perineal exam using the perineal elasticity meter present herein provides a more surfacial exam (e.g., measuring elasticity properties of the middle third of the vagina) and does not have contact with the uterine cervix.

Of course, this equipment can be made using various materials, sizes and colors as will be understood by one of skill in the art.

The invention claimed is:

1. A perineal elasticity meter comprising:
   a circular central stem, wherein the circular central stem includes measurement markings on an exterior, distal portion;
   a sleeve slidably surrounding at least part of the distal portion of the central stem, wherein the sleeve comprises an opening through which a portion of the markings can be viewed;
   a ring surrounding a proximal portion of the central stem;
   a plurality of arms extending radially from the ring;
   a plurality of expanders extending circumferentially from the circular central stem, wherein the plurality of expanders are each connected to the ring via the plurality of arms extending radially from the central stem;
   a first plurality of hinges connected between the plurality of arms and the ring; and
   a second plurality of hinges connected between each of the plurality of arms and a corresponding one of the plurality of expanders,
   wherein the sleeve is positioned adjacent to the expanders such that as the sleeve slidably moves toward the proximal end of the perineal elasticity meter, the sleeve causes the expanders to expand in a direction opposite the central stem.

2. The perineal elasticity meter according to claim 1, further comprising:
   a second ring surrounding the central stem at a position between the ring and the sleeve;
   a second plurality of arms extending radially from the second ring;
   a third plurality of hinges connected between the second plurality of arms and the second ring; and a fourth plurality of hinges connected between each of the second plurality of arms and a corresponding one of the plurality of expanders.

3. The perineal elasticity meter according to claim 2, wherein the plurality of arms each connect to a corresponding one of the plurality of expanders at a proximal end of the corresponding expander and the second plurality of arms each connect to a corresponding one of the plurality of expanders at a distal end of the corresponding expander.

4. The perineal elasticity meter according to claim 3, further comprising:
   a third plurality of arms provided between the sleeve and a corresponding one of the second plurality of arms.

5. The perineal elasticity meter according to claim 4, further comprising:
   a fifth plurality of hinges connected between the third plurality of arms and the second ring; and
   a fourth plurality of hinges connected between the second plurality of arms and the sleeve.

6. The perineal elasticity meter according to claim 5, wherein pressure applied to move the sleeve toward the proximal portion of the central stem is communicated to the third plurality of arms and is further applied via the third plurality of arms to the second ring.

7. The perineal elasticity meter according to claim 6, wherein pressure applied to move the sleeve toward the proximate portion of the central stem is further communicated via the second ring to the second plurality of arms thereby causing the plurality of expanders to expand away from the central stem.

8. The perineal elasticity meter according to claim 7, wherein the opening in the sleeve is provided to allow a view of the portion of the markings corresponding to a current diameter between opposite expanders.

9. The perineal elasticity meter according to claim 8, wherein the opening provides a measurement of the perineal elasticity of a patient.

* * * * *

UNITED STATES PATENT AND TRADEMARK OFFICE
CERTIFICATE OF CORRECTION

PATENT NO. : 8,512,261 B2  
APPLICATION NO. : 12/666719  
DATED : August 20, 2013  
INVENTOR(S) : Miriam Zanetti et al.

Page 1 of 1

It is certified that error appears in the above-identified patent and that said Letters Patent is hereby corrected as shown below:

On the Title Page

Item (30)  Foreign Application Priority Data  
           Jun. 26, 2007   (BR)................................0702130 should read -- Jun. 26, 2007   (BR).............................0702130  
           May 27, 2008   (BR).............................018080032067 --

Signed and Sealed this  
Fifth Day of November, 2013

Teresa Stanek Rea  
*Deputy Director of the United States Patent and Trademark Office*